US006303910B2

(12) United States Patent
Glucksman et al.

(10) Patent No.: US 6,303,910 B2
(45) Date of Patent: Oct. 16, 2001

(54) METHOD OF MAKING AN INJECTION MOLDED PARAFFIN BATH AND APPARATUS MADE THEREBY

(75) Inventors: Dov Glucksman, Wemham, MA (US); Roman S. Ferber, West Bloomfield, MI (US)

(73) Assignee: HoMedics, Inc., Commerce Twsp., MI (US)

( * ) Notice: Subject to any disclaimer, the term of this patent is extended or adjusted under 35 U.S.C. 154(b) by 0 days.

(21) Appl. No.: 09/776,796

(22) Filed: Feb. 5, 2001

Related U.S. Application Data

(63) Continuation-in-part of application No. 09/523,506, filed on Mar. 10, 2000, now Pat. No. 6,184,500.

(51) Int. Cl.[7] ................................ A61F 7/00; A61K 7/50; H05B 3/02; H05B 3/16

(52) U.S. Cl. ............................ 219/430; 219/436; 607/86; 607/114; 4/545

(58) Field of Search ..................................... 219/430, 436, 219/438, 439, 521, 530, 536; 607/86, 89, 114; 4/545

(56) References Cited

U.S. PATENT DOCUMENTS

| | | | |
|---|---|---|---|
| 1,319,559 * | 10/1919 | Bjorkholm et al. | 219/436 |
| 1,390,719 * | 9/1921 | Lozano | 219/436 |
| 2,463,329 | 6/1947 | Stansbury . | |
| 2,904,037 | 9/1959 | Cassidy . | |
| 3,834,459 | 9/1974 | Layton . | |
| 3,892,945 | 7/1975 | Lerner . | |
| 3,985,511 * | 10/1976 | Betts | 219/437 |
| 4,052,590 * | 10/1977 | Anderl et al. | 219/438 |
| 4,204,110 | 5/1980 | Smit et al. . | |
| 4,272,673 | 6/1981 | Semanez et al. . | |
| 4,325,254 | 4/1982 | Svacina et al. . | |
| 4,485,297 | 11/1984 | Grise et al. . | |
| 4,513,735 | 4/1985 | Friedson et al. . | |
| 4,632,115 | 12/1986 | Bernardini . | |
| 4,640,226 * | 2/1987 | Liff | 119/69.5 |
| 4,656,339 | 4/1987 | Grise . | |
| 4,696,303 | 9/1987 | Bernardini . | |
| 4,782,835 | 11/1988 | Bernardini . | |
| 4,814,586 | 3/1989 | Grise . | |
| 4,860,434 | 8/1989 | Louison et al. . | |
| 4,880,415 | 11/1989 | Urakami . | |
| 4,937,435 | 6/1990 | Goss et al. . | |
| 4,967,061 | 10/1990 | Weber, Jr. et al. . | |
| 5,345,063 * | 9/1994 | Reusche et al. | 219/436 |
| 5,508,494 | 4/1996 | Sarris et al. . | |
| 5,588,161 * | 12/1996 | Barradas | 607/86 |
| 5,674,268 | 10/1997 | Riazi . | |
| 5,693,244 | 12/1997 | Pragt et al. . | |
| 5,700,284 | 12/1997 | Owens . | |
| 5,702,623 | 12/1997 | Sharples . | |
| 5,914,063 | 6/1999 | Taylor et al. . | |

FOREIGN PATENT DOCUMENTS

| | | |
|---|---|---|
| 61-65815 | 4/1986 | (JP) . |
| 11-56893 | 3/1999 | (JP) . |

OTHER PUBLICATIONS

TheraBath® Paraffin Wax Therapy for arthritis, bursitis, tendonitis, www.1rehab.com/paraffin/index.htm, May 23, 2000, pp. 1–3.

Remington Products, Hand Care, www.remington–products.com/products/spatherapy/ahdn.html, May 23, 2000, pp. 1–3.

Photographs of Gena Paraffin Bath Product, pp. 1–2.

ParaTherm Product Manufactured by Grimm Scientific Industries, pp. 1–5.

* cited by examiner

*Primary Examiner*—Joseph Pelham
(74) *Attorney, Agent, or Firm*—Brooks & Kushman P.C.

(57) ABSTRACT

A paraffin bath apparatus has injection molded components including an inner tub, housing, base, control panel, and lid. The inner tub is provided with paired flanges on its bottom surface to which a wire heating element is assembled and secured. Wire guides are provided on the upstanding wall of the inner tub to which a side heating wire is assembled and secured by means of wire guides and an adhesive coated foil segment.

17 Claims, 3 Drawing Sheets

METHOD OF MAKING AN INJECTION MOLDED PARAFFIN BATH AND APPARATUS MADE THEREBY

CROSS-REFERENCE TO RELATED APPLICATIONS

This application is a continuation-in-part of U.S. application Ser. No. 09/523,506, filed Mar. 10, 2000, now U.S. Pat. No. 6,184,500, which is incorporated by reference herein.

TECHNICAL FIELD

The present invention relates to a method of making a paraffin bath and to a paraffin bath apparatus made according to the method.

BACKGROUND ART

A paraffin bath is an appliance that is used to melt paraffin for therapeutic purposes. Warm paraffin wax melted in the bath is used to treat dry, chapped hands and may provide pain relief for stiff or aching joints that may be caused by bursitis and arthritis.

Paraffin baths are known that include a metal inner tub in which the paraffin wax is melted. Paraffin baths made of metal are relatively expensive to manufacture and can be dented if improperly handled.

Applicants' assignees' prior paraffin bath of application Ser. No. 09/523,506 discloses a method of making a paraffin bath having a plastic inner tub and having heating elements that comprise braided wire sandwiched between layers of foil that are assembled to the side walls of the inner tub and base wall of the inner tub.

The prior art also includes devices such as foot baths that have a rope heater attached to integrally formed flanges on a base wall. An example of such a device is disclosed in U.S. patent application Ser. No. 09/631,643, filed Aug. 2, 2000 that is assigned to the assignee of this application. The prior art foot baths do not have side wall mounted heating elements and are intended to heat water or at least prevent previously heated water from cooling down.

There is a need for a paraffin bath in which all major structural components are formed by a simple, reliable and inexpensive process. For example, there is a need for a paraffin bath manufactured from structural parts that are injection molded of a temperature resistant plastic such as polypropylene. There is also a need for a manufacturing process utilizing injection molded parts that are assembled with a heating element and controller in an efficient and cost effective manner. There is also a need for a simple, durable paraffin bath appliance that is inexpensive to manufacture.

These and other problems and objectives are addressed by applicant's invention as will be summarized below.

DISCLOSURE OF INVENTION

According to the present invention, a paraffin bath apparatus for melting paraffin is disclosed that has a housing having a base wall, side wall and an upper opening. A polymeric inner tub is received within the housing and is a generally cup-shaped member having a bottom wall, an upstanding wall and an open top. The inner tub is received within the upper opening of the housing with the bottom wall overlying the base wall of the housing. A heating element is mounted on an outer wall of the inner tub between the inner tub and the housing. The heating element provides heat through the inner tub that is sufficient to melt the paraffin but is limited to a temperature that is below the temperature that would adversely effect the polymeric material of the inner tub. The heating element comprises a wire that is at least partially retained in a series of loops between paired flanges that are integrally molded of the same polymeric material forming the inner tub walls. The paired flanges are spaced apart to receive the wire. A thermostat is electrically connected to the heating element to control the heat provided to the inner tub.

According to another aspect of the invention, the heating element includes a base heating element that is located between the base wall of the housing and the bottom wall of the inner tub. A side heating element is located between the side wall of the housing and the upstanding wall of the inner tub. The base heating element is received by flanges formed on the bottom wall of the inner tub.

According to a further aspect of the invention, a thermostatic sensor is remotely mounted on the inner tub and is connected to a thermally conductive element that is coated with a refractive sealant that provides a heat conduction path between the thermally conductive element and the base wall of the inner tub.

According to yet another aspect of the invention, at least one metal wire guide is provided on the upstanding wall of the inner tub that has projections extending outwardly from the upstanding wall. The heating element is wrapped around the upstanding wall and retained by the projections. At least one layer of adhesive coated foil is wrapped around the wire after the wire is wrapped around the upstanding wall and the metal wire guide.

According to another aspect of the invention the major structural parts of the paraffin bath are all formed of polypropylene. The housing, a control panel, base and removable lid all may be formed of polypropylene.

A thermostat or other electronic temperature control circuit is assembled to one or both of the inner tub and the control panel. The control panel is attached to an opening formed in part by the inner tub and in part by the housing.

According to the method of the present invention, a method of making a molded polymeric paraffin bath appliance is provided. A housing is provided that has a base wall and a side wall defining an upper opening. An inner tub is injection molded and includes a base having inner and outer sides and a wall extending from the base to an upper opening. A plurality of wire retainer flanges are simultaneously molded on the outer side of the base of the inner tub. A wire is assembled to the wire retainer flanges. The wires are connected to a voltage source and the voltage source is connected to a controller for controlling the current provided to the voltage source and thereby control the heat generated by the wire. The inner tub is assembled to the housing to provide an enclosed space between the inner tub and the outer tub for containing the wire heating element.

According to another aspect of the method of the present invention, at least some of the flanges are deformed by partially melting the flanges after the wire is assembled to the flanges to retain the wire within the flanges.

According to a further aspect of the method of the invention, the housing is injection molded of a polymeric material. The base is also injection molded and assembled to the housing. The control panel is molded of polymeric material. A temperature controller is attached to a heat transfer element that is mounted on the inner tub before the control panel is attached to the housing. A removable lid is also injection molded of polymeric material and is adapted to be removably placed on the upper opening of the housing.

According to yet another aspect of the method of the invention, at least one wire guide is assembled to the outer surface of the wall of the inner tub. A wire is wrapped around the inner tub a plurality of times with the wire guide retaining the wire. Foil having an adhesive coating is wrapped around the inner tub over the wire and wire retainer so that it adheres to portions of the wire and the inner tub to hold the wire on the inner tub. The foil also functions to disperse heat from the wire about the sides of the inner tub. The wire is connected to the voltage source as previously described.

These and other aspects and advantages of the invention will be better understood in view of the attached drawings and following detailed description of the invention.

BEST MODE FOR CARRYING OUT THE INVENTION

Figure 1:
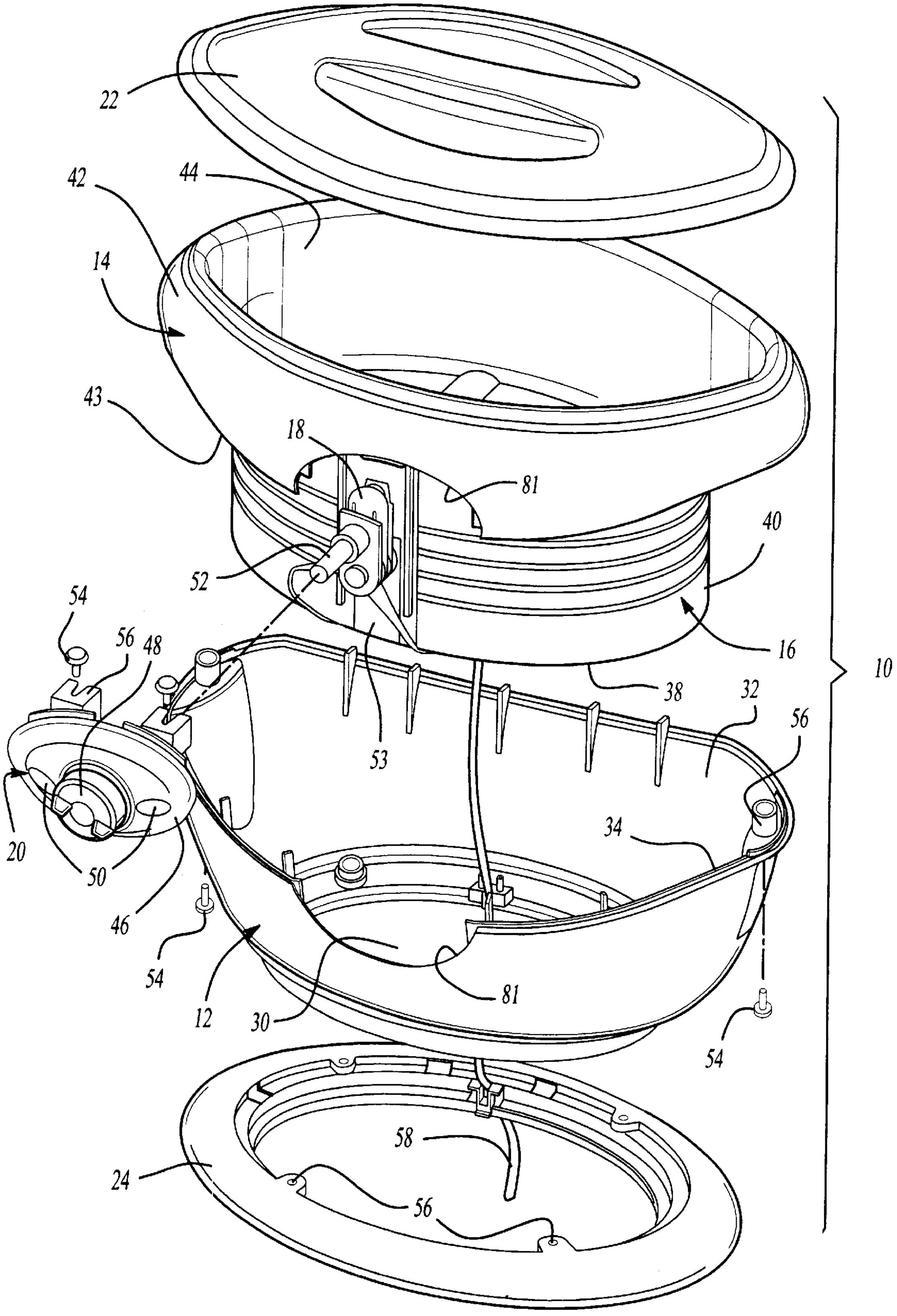
FIG. 1 is an exploded perspective view of a paraffin bath apparatus made according to the present invention.

Referring to FIG. 1, a paraffin bath apparatus 10 is illustrated in exploded perspective. The paraffin bath apparatus 10 includes a housing 12 and an inner tub 14. A heating element 16 is assembled to the inner tub 14. Heating element 16 is connected to a thermostat 18 that controls the current provided to the heating element 16. The thermostat 18 may be a bimetal strip, thermistor, solid-state temperature control circuit, or the like. A control panel 20 is assembled to the housing 12 and inner tub 14. A lid 22 is provided to cover paraffin contained in the paraffin bath apparatus 10. A base 24 is secured to the housing 12 to stabilize the paraffin bath apparatus 10.

The housing 12 includes a base wall 30 from which a generally oval side wall 32 extends upwardly. The side wall 32 defines on its upper end an upper opening 34.

Figure 2:
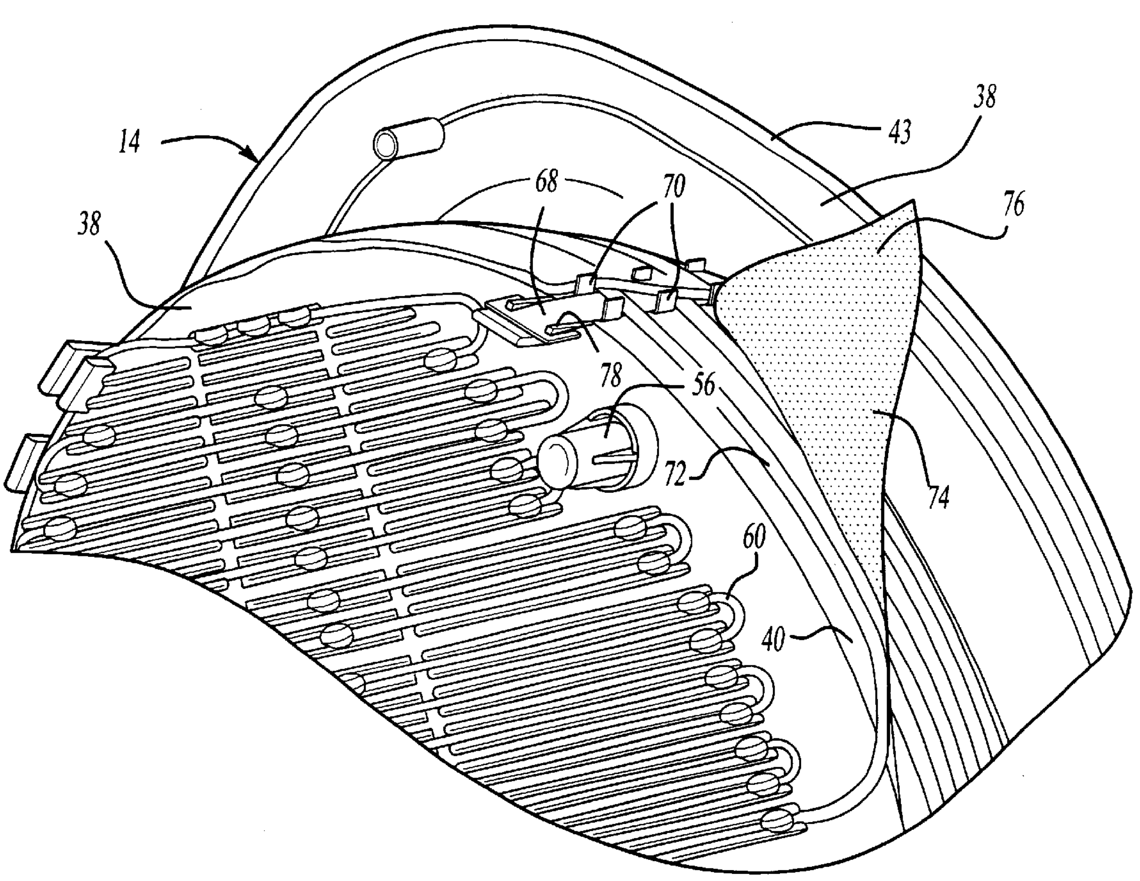
FIG. 2 is a fragmentary bottom perspective view of an inner tub and heating element thereof.

Referring now to FIGS. 1 and 2, the inner tub 14 includes a bottom wall 38 and an upstanding wall 40. The upstanding wall 40 is generally oval shaped and extends substantially vertically upwardly from the bottom wall 38. The upstanding wall 40 defines a rim 42 at its uppermost portion that is reversely turned and extends outwardly and downwardly from the rim 42 and terminates in a downwardly facing edge 43 that is adapted to be joined to the upper opening 34 of the housing 12. Within the rim, an oval, cup-shaped vessel 44 is defined in which solid paraffin is placed to be melted in the paraffin bath apparatus 10.

Figure 3:
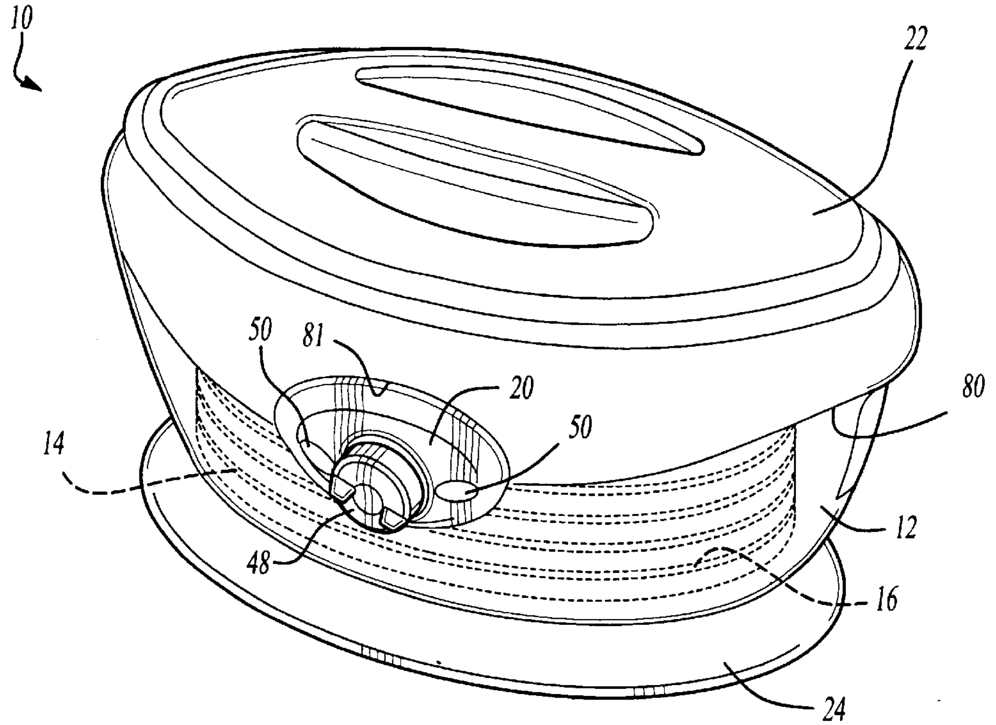
FIG. 3 is a front perspective view of a paraffin bath apparatus made according to the present invention.

Referring to FIGS. 1 and 3, a face plate 46 forms part of the control panel 20. A knob 48 forms part of the control panel 20 as well as indicator lights 50. The indicator lights 50 may be used to indicate whether or not the power is on and whether or not the heater element is on or off. The knob 48 is connected to a shaft 52 that extends from the thermostat 18. The knob 48 is provided to allow the temperature of the paraffin to be controlled through the thermostat within a range of potentially desirable temperatures. The thermostat 18 is remote from the inner tub and is connected to a thermally conductive element 53.

The components of the paraffin bath apparatus 10 are assembled by means of fasteners 54, such as screws, that are received in receptacle 56 formed at corresponding locations on the various components of the paraffin bath apparatus. Receptacles may be threaded or, if the fasteners 54 are self-tapping fasteners, receptacles 56 may be molded members having holes sized to accept the fasteners 54. A power cord 58 is provided to allow the unit to be plugged into a wall receptacle.

Referring now to FIGS. 1 and 2, the heating system of the paraffin bath apparatus 10 will be described in greater detail. The heating element 16 includes a base heating wire 60 that is secured to the bottom wall 38 of the inner tub 14. The base heating wire 60 extends in a serpentine path and is retained between sets of paired flanges 62 that are integrally formed on the bottom side of the bottom wall 38. The base heating wire 60 is inserted between the paired flanges 62 and is permanently retained therein by means of deformations 64 that are formed by partially melting the flanges 62 at spaced locations. The deformations 64 may be formed by contacting the paired flanges 62 with a heated member.

Referring now to FIG. 2, a plurality of wire guides 68 are provided at spaced locations on the outside of the upstanding wall 40 of the inner tub 14. The wire guides 68 have teeth 70 that extend outwardly from the wire guides 68. A side heating wire 72 is wrapped around the upstanding wall 40 and is retained by the teeth 70 of the wire guides 68. After the side heating wire 72 has been wound around the wire guides 68 and upstanding wall 40, a metallic foil sheet 74 is wrapped around the outside thereof. The foil 74 may be coated on one side with a pre-applied pressure sensitive adhesive 86 that causes the foil 74 to adhere to the wire guides 68 and retain the side heating wire 72 in place on the upstanding wall 40. The foil 74 also functions to disperse heat generated in the side heating wire 72. The wire guides 68 are received in one or more integrally formed clips 78.

The rim 42 of the inner tub 14 preferably defines integrally formed handles 80 that are used to grip or carry the paraffin bath apparatus 10. The handles 80 may take various forms. Preferably, a pair of handles 80 are provided on opposite lateral sides of the paraffin bath apparatus 10 to provide a convenient way to carry the paraffin bath apparatus 10.

The control panel 20 is preferably received between the edge of upper opening 34 of the housing 12 and the downwardly facing edge 43 of the inner tub 14. An opening 81 formed partially in the edge 43 and partially in the side wall 32 of the housing receives the control panel 20.

Figure 4:
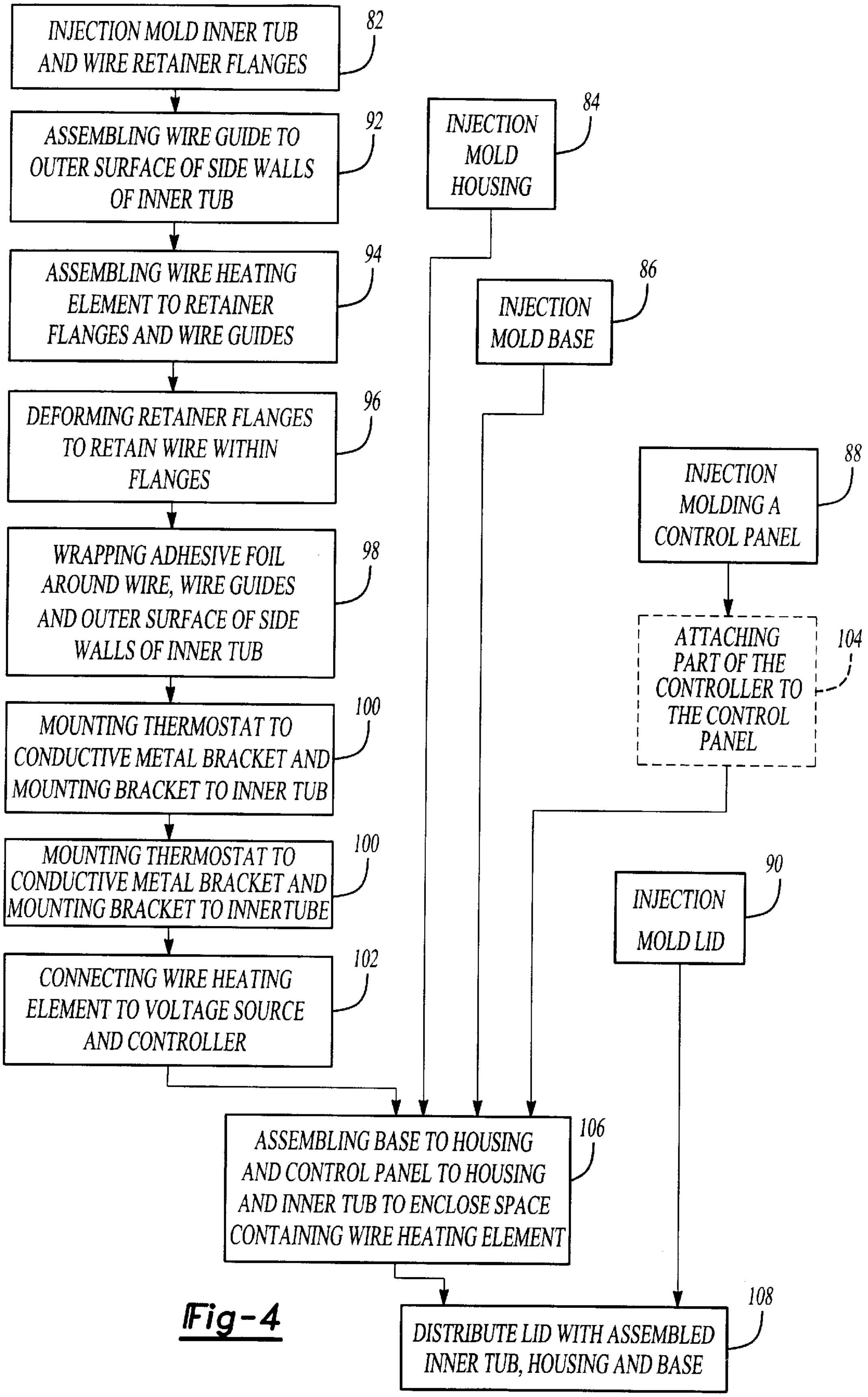
FIG. 4 is a process flowchart illustrating one embodiment of a process for manufacturing a paraffin bath apparatus according to the present invention.

Referring now to FIG. 4, an exemplary process illustrating one potential combination of steps in the method of manufacturing a paraffin bath apparatus 10 is illustrated. It should be understood that additional steps may be added, some steps omitted, or changes in the order of the steps may be made without departing from the spirit and scope of the invention.

Referring now to FIG. 4, the inner tub is injection molded at 82. During the molding step, wire retainer flanges are formed on the bottom wall 38. If desired, wire retainer flanges could also be provided on the upstanding wall 40. The housing 12 is injection molded at 84 and the base 24 is injection molded at 86. A control panel 20 is injection molded at 88 and the lid 22 is injection molded at 90. It is one feature of the method of the invention that all of the large structural components of the paraffin bath apparatus 10 are injection molded thereby providing a durable product and a cost-effective manufacturing process.

After the inner tub is injection molded at 82, one or more wire guides 68 are assembled to the outer surface of the upstanding wall 40 of the inner tub 14 at reference numeral 92. The base heating wire 60 is then assembled to the retainer flanges, or wire guide 68 and paired flanges 62 on the bottom wall 38 at 94. The retainer flanges may then be deformed by partially melting the flanges 62 to retain the base heating wire 60 at 96. Adhesive 76 coated foil 74 is wrapped at 98 around the wires 72 and outer surface of the upstanding wall 40 of the inner tub 14. The foil 74 may have adhesive applied to it as a separate step or it may be provided in a tape-like form with pressure sensitive adhesive being pre-applied. The thermostat 18 is mounted on the inner tub 14 and is connected to the thermally conductive element 53 that is in turn secured to the bottom wall 38 of the inner tub 14 at reference numeral 100. The wire heating element is connected to a voltage source and controller at reference numeral 102.

The control panel is injection molded at 88 and may be further processed in subassembly operations such as attaching a portion of the controller, wiring LEDs, or other indicator lights as a preliminary step to final assembly at 104. Final assembly occurs at reference numeral 106 wherein the base 24 is assembled to the housing 12 in inner tub 14 and the control panel 20. The inner tub 14 subassembly is assembled to the housing 12 thereby enclosing the space containing the heating element 16 between the inner tub 14 and the housing 12. Finally at 108, the removable lid 22 is assembled to the paraffin bath apparatus 10 for distribution.

The controller may be assembled to either the control panel, inner tub, or housing depending upon the desired manufacturing process to be selected.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A paraffin bath apparatus for melting paraffin comprising:

a housing having a base wall and a side wall defining an upper opening;

a polymeric inner tub that is generally cup shaped having a bottom wall and an upstanding wall defining an open top, the inner tub being received within upper opening of the housing with the bottom wall overlying the base wall, the inner tub being adapted to contain melted paraffin;

a heating element is disposed between the inner tub and the housing, the heating element providing heat through the inner tub sufficient to melt the paraffin but below the temperature that would adversely effect the polymeric material forming the inner tub, the heating element comprising a wire at least partially retained in a series of loops between paired flanges that are integrally molded of the same polymeric material forming the inner tub walls, the paired flanges being spaced apart to receive portions of the wire; and a thermostat electrically connected to the heating element to control the heat provided to the inner tub.

2. The paraffin bath apparatus of claim 1 wherein the heating element includes a base heating wire located between the base wall and the bottom wall and a side heating wire located between the side wall and the upstanding wall, the base heating wire being received by flanges formed on the base wall.

3. The paraffin bath apparatus of claim 1 wherein an injection molded base is separately formed from the housing and assembled to the housing.

4. The paraffin bath apparatus of claim 1 wherein a thermostat is remotely mounted relative to the inner tub and is connected to a thermally conductive element.

5. The paraffin bath apparatus of claim 1 wherein at least one metal wire guide is provided on the upstanding wall that has teeth extending outwardly from the upstanding wall, wherein the heating element is wrapped around the upstanding wall and retained by the projections.

6. The paraffin bath apparatus of claim 5 wherein the wire is wrapped around the upstanding wall and the metal wire guide and wherein at least one layer of adhesive coated foil is wrapped around the wire after the wire is wrapped around the upstanding wall and metal wire guide.

7. The paraffin bath apparatus of claim 1 wherein the polymeric material forming the inner tub is polypropylene.

8. The paraffin bath apparatus of claim 1 wherein the housing is injection molded from polypropylene.

9. The paraffin bath apparatus of claim 1 wherein a control panel is injection molded and a temperature controller is assembled to the inner tub and wherein the control panel is attached to an opening formed in part by the inner tub and formed in part by the housing.

10. A method of making a paraffin bath appliance comprising:

providing a housing having a base wall, a side wall and an upper opening;

injection molding an inner tub having a base having inner and outer sides and a wall extending from the base to an upper opening, and simultaneously molding a plurality of wire retainer flanges on the outer side of the base;

assembling a wire to the wire retainer flanges;

connecting the wire to a controller for controlling the heat generated by the wire; and assembling the inner tub to the housing and thereby enclosing a space between the inner tub and housing that contains the wire.

11. The method of claim 10 further comprising the step of deforming the flanges after the wire is assembled to the flanges to retain the wire within the flanges.

12. The method of claim 10 further comprising the step of injection molding the housing of polymeric material.

13. The method of claim 10 further comprising the step of assembling at least one wire guide to the outer surface of the wall of the inner tub and wrapping a second wire a around the inner tub plurality of times with the wire guide retaining the second wire, and connecting the second wire to the voltage source.

14. The method of claim 13 further comprising the step of coating a segment of foil with an adhesive and wrapping the segment of foil around the inner tub over the second wire and wire guide adhering the segment of foil to portions of the wire and inner tub to hold the wire on the inner tub and also disperse heat from the wire about the sides of the inner tub.

15. The method of claim 10 further comprising the steps of injection molding a base and assembling the base to the housing.

16. The method of claim 10 further comprising injection molding a removable lid that is adapted to be placed on the upper opening of the housing.

17. The method of claim 10 further comprising injection molding a control panel and attaching the controller to the inner tub before attaching the control panel to the controller, the housing and the inner tub.

* * * * *